United States Patent [19]
Pressly et al.

[11] Patent Number: 5,211,629
[45] Date of Patent: May 18, 1993

[54] SAFETY SYRINGE

[76] Inventors: William B. S. Pressly, 112 Caedmon Ct., Greer, S.C. 29650; Charles A. Vaughn, Sr., 3123 Queens Walk NE., Atlanta, Ga. 30345

[21] Appl. No.: 813,115

[22] Filed: Dec. 23, 1991

[51] Int. Cl.$^5$ .............................................. A61M 5/00
[52] U.S. Cl. ..................................... 604/110; 604/195
[58] Field of Search ............... 604/110, 195, 187, 263, 604/198

[56] References Cited

U.S. PATENT DOCUMENTS

| | | | |
|---|---|---|---|
| 4,838,869 | 6/1989 | Allard | 604/195 |
| 5,019,044 | 5/1991 | Tsao | 604/110 |
| 5,053,010 | 10/1991 | McGary et al. | 604/195 X |
| 5,064,419 | 11/1991 | Gaarde | 604/195 |
| 5,114,410 | 5/1992 | Batlle | 604/195 |

*Primary Examiner*—John D. Yasko
*Attorney, Agent, or Firm*—John B. Hardaway, III; Jeffrey L. Wilson; J. Bennett Mullinax

[57] ABSTRACT

A hypodermic syringe is provided having a barrel with a movable plunger therein to inject a fluid through a hollow needle thereof which is housed within a passageway of a needle assembly that is attached to the barrel by ultrasonic welding means or other permanent attaching means. Positioned between sacrificial supports in the needle assembly and the barrel is a deformable base. The deformable base houses an enlarged head of the needle which is in contact with energy storage means within the passageway of the needle assembly. The plunger has a rupturable boot thereon which, upon completion of an injection, contacts a deformable base forcing it downward and severing a sacrificial support means within the needle assembly thereby permitting the base to move the enlarged head of the needle downward, until it is blocked by the passageway. Further movement of the base forces the enlarged needle head from the base and into contact with the rupturable boot. Movement of the base continues until the rupturable boot is ruptured by the enlarged head of the needle and the enlarged head of the needle is released from the base thereby triggering a projection of the needle into a hollow portion of the plunger by transfer of energy from energy storage means. Once inside the plunger, the needle is trapped by its enlarged head within the plunger, and the plunger is locked into the body of the syringe.

13 Claims, 6 Drawing Sheets

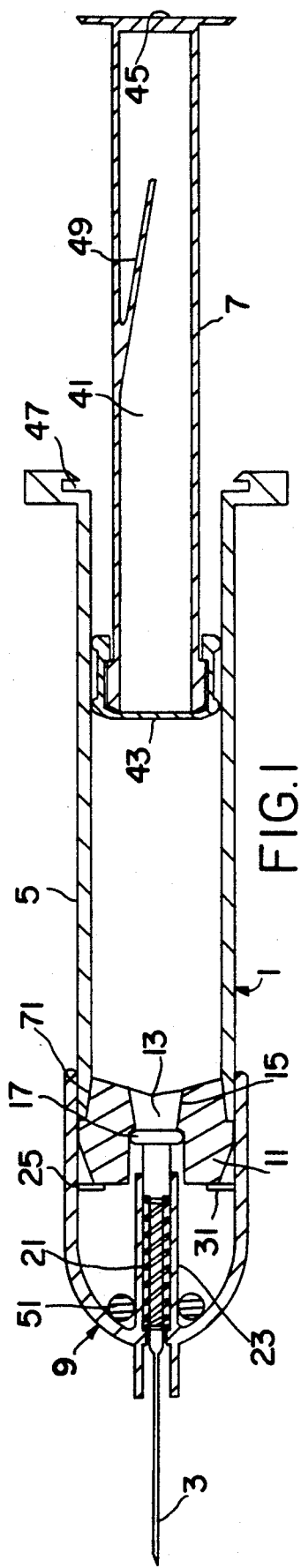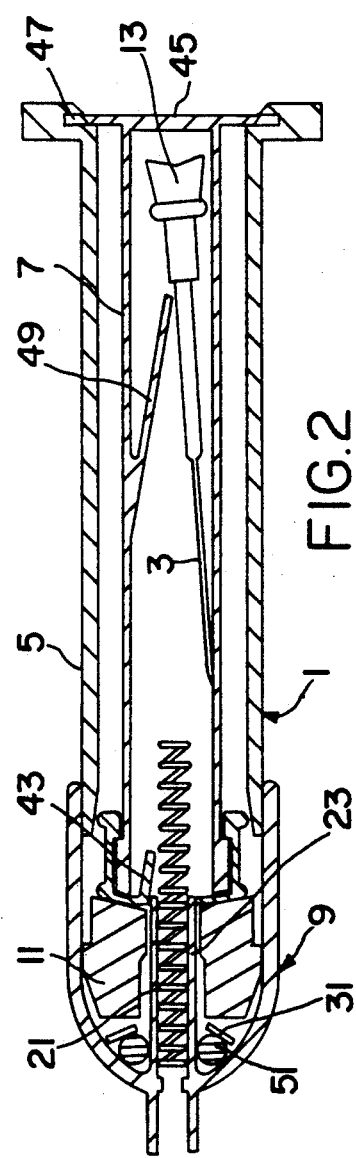

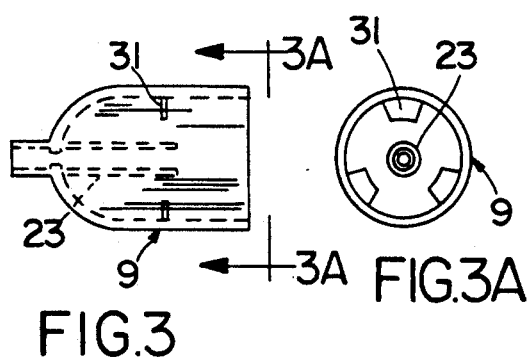
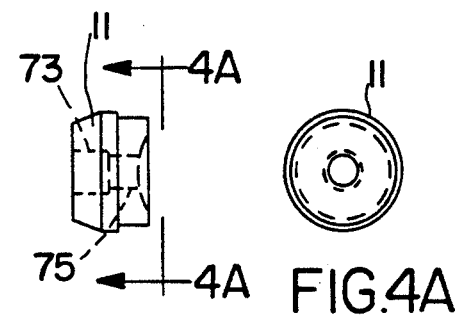
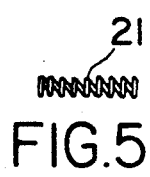
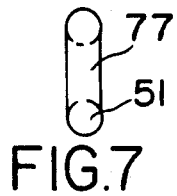
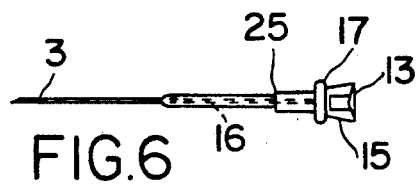
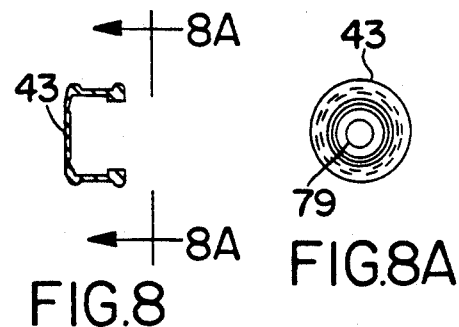
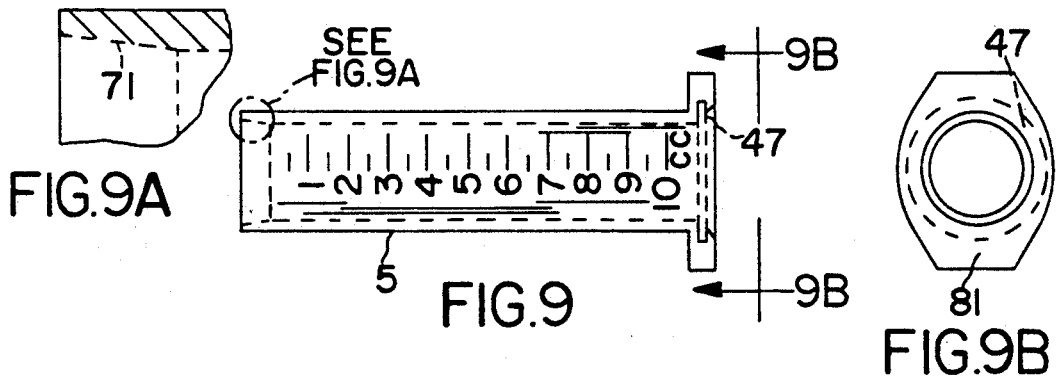
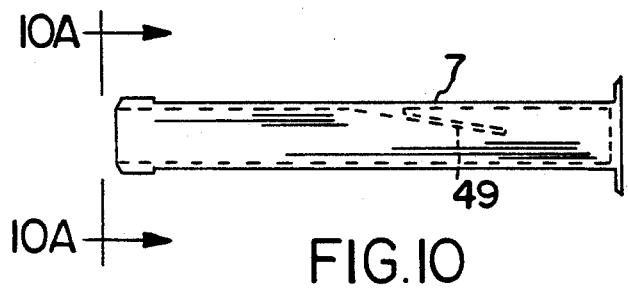
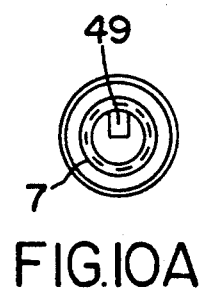

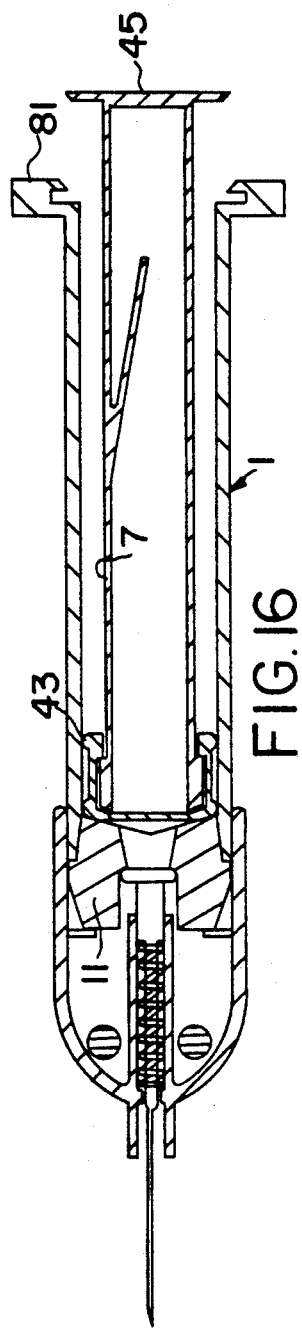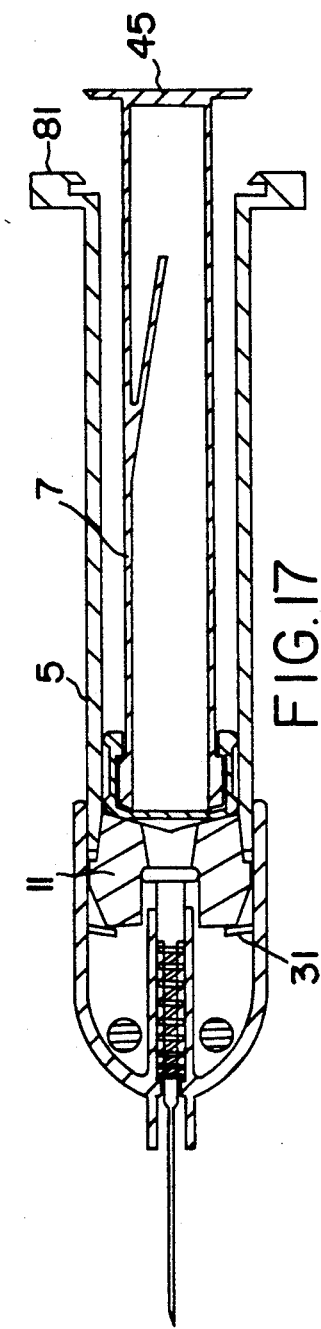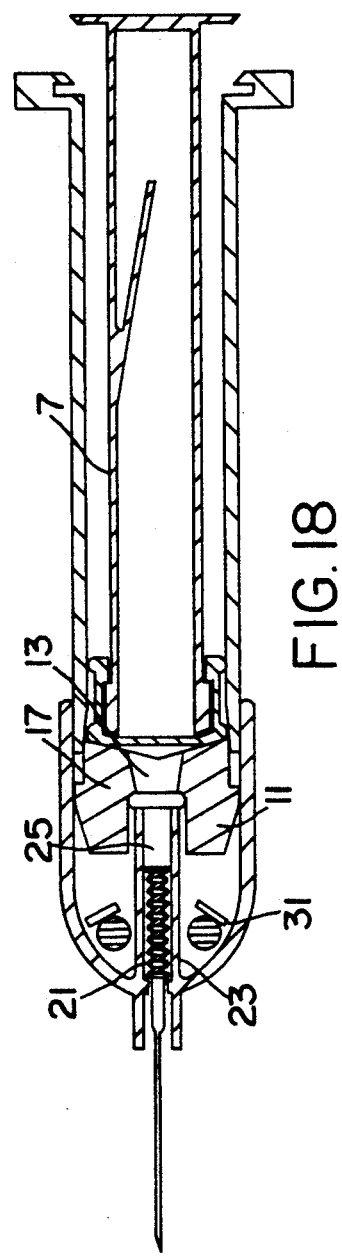

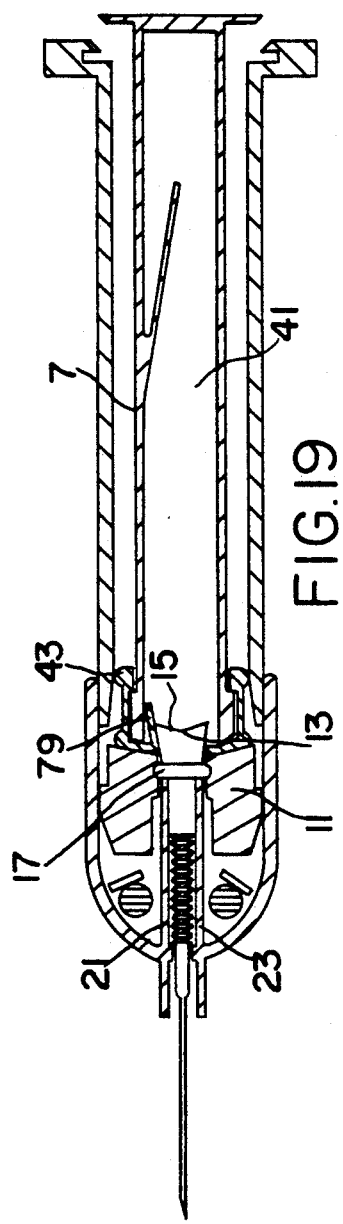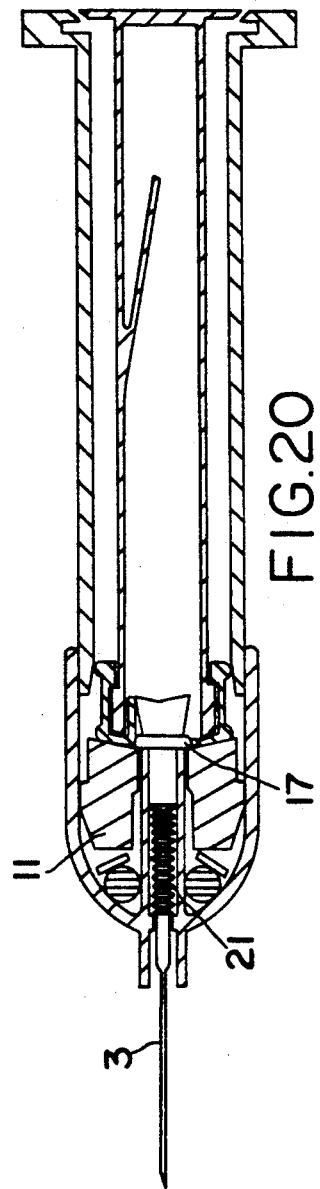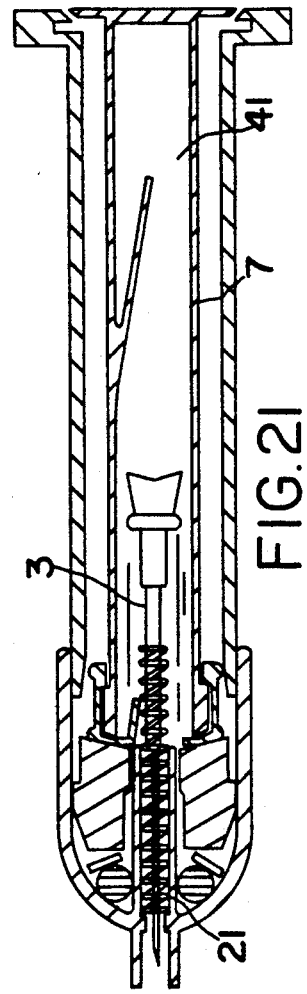

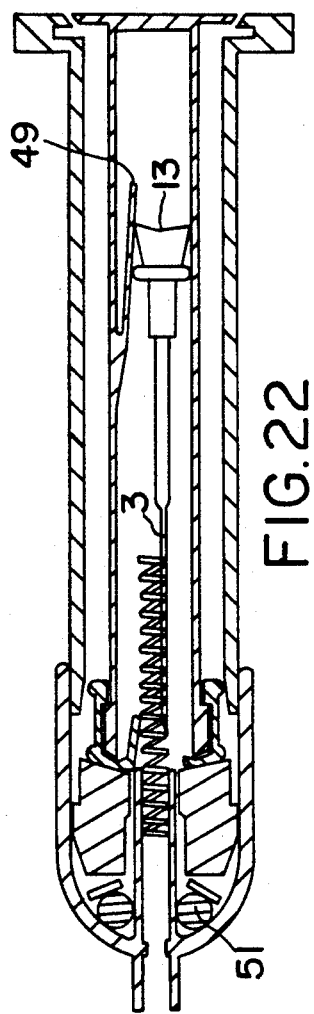
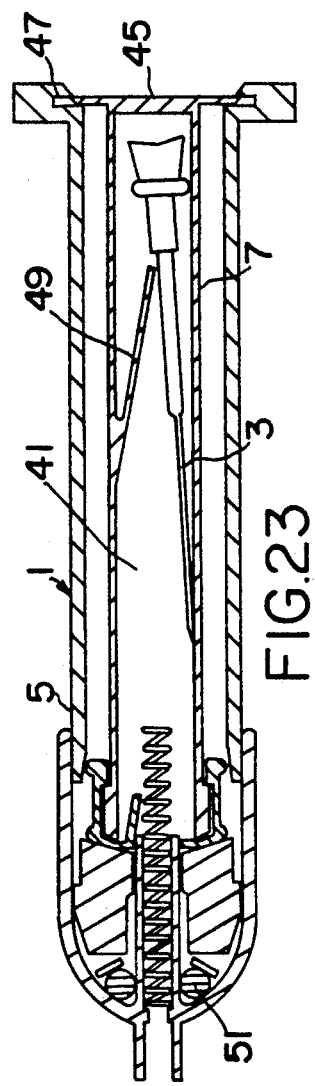
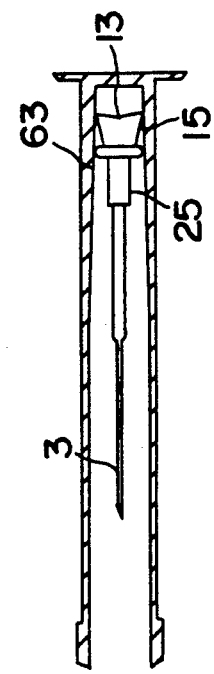
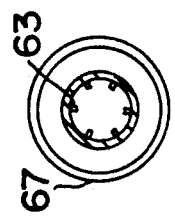
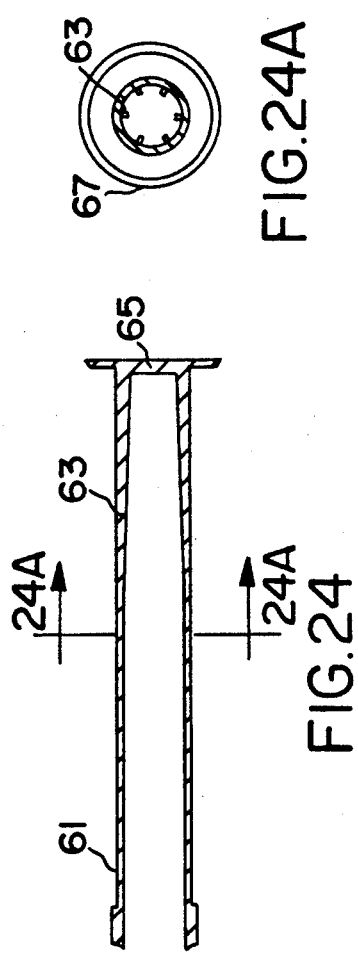

SAFETY SYRINGE

BACKGROUND OF THE INVENTION

This invention relates generally to the art of syringes and more particularly to a syringe which reduces the likelihood of unintentional puncture or pricking of human skin. In recent history, the transmission of contagious diseases, particularly those brought about exclusively by the co-mingling of human body fluids, has been of great technological interest. One of the particular problems has been associated with the use and disposal of hypodermic syringes, particularly among healthcare professionals. There have been various devices developed for the destruction of the needles or cannula used in such syringes. Additional devices have been developed for capping of syringes which attempt to minimize the likelihood of accidental puncture. The accidental puncture or pricking of a finger, or any other part of the body, after the treatment of a patient with a contagious disease, particularly a deadly contagious disease, results in a high likelihood of transmission of that disease. Various syringes have been developed in the prior art to attempt to minimize the likelihood of accidental puncture after patient treatment.

One such device is described in U.S. Pat. No. 4,973,316 to Dysarz wherein a needle is retracted into the barrel of the syringe after the use thereof. Another such device is described in U.S. Pat. No. 4,921,486 to DeChellis, et al. One of the earlier patents in this regard was U.S. Pat. No. 2,460,039 issued to Scherer, et al. Various other prior art devices exist as well in the patent literature. While all such devices seek the same goal of preventing accidental puncture, considerable room for improvement exists.

SUMMARY OF THE INVENTION

It is thus an object of this invention to provide a novel hypodermic syringe which minimizes the likelihood of accidental puncture.

It is a further object of this invention to provide such a syringe which, after utilization, isolates the used needle so as to render such needle harmless.

It is a further and more particular object of this invention to provide such a hypodermic syringe which is operable utilizing only one hand.

It is a further and yet more particular object of this invention to provide such a syringe which automatically, upon the end of an injection, renders such needle harmless, purposely destroys parts of the syringe, and prevents its reuse.

It is a further object of the invention to provide a simple device, which is easily manufacturable.

These as well as other objects are accomplished by a hypodermic syringe having a barrel with a movable plunger therein to inject a fluid through a hollow needle thereof. A hollow needle is housed in a passageway within a needle assembly. Positioned between sacrificial support means in the needle assembly and an internal wedged end of the barrel is a deformable base which forms a liquid tight seal with the barrel, at the needle end of the barrel. The deformable base houses an enlarged head of the needle which enlarged head is in contact with energy storage means within the passageway in the needle assembly. The plunger has a rupturable boot thereon which is otherwise liquid impermeable for forcing a liquid from the barrel upon movement of the plunger. Upon completion of an injection, the rupturable boot contacts the deformable base, and upon application of force at the plunger, moves such base downward, initially breaking the liquid tight seal between the deformable base and the barrel. Continued application of force causes sacrificial support means within the needle assembly to sever, permitting the deformable base to move the enlarged head of the needle downward until further movement of the enlarged head is blocked by the passageway in the needle assembly. With the enlarged needle head blocked by the passageway, continued force at the plunger causes the deformable base to move around the enlarged needle head. As the deformable base moves forward, the enlarged needle head begins to protrude from the deformable base and come into contact with a thin web on the rupturable boot of the plunger. Continued force causes the enlarged needle head to penetrate the rupturable boot, positioning the enlarged needle head just inside a hollow portion of the plunger. As the plunger moves the deformable base still further, the enlarged needle head looses contact with the deformable base, which triggers a release of energy from the energy storage means in the passageway, projecting the needle into the hollow portion of the plunger. Once inside the plunger, the needle is trapped by its enlarged head within the plunger. Final movement of the plunger causes the plunger to become locked in the barrel at the back of the syringe.

BRIEF DESCRIPTION OF THE DRAWINGS

FIG. 1 of the drawings is a cross-sectional view of the syringe of this invention in its operable state.

FIG. 2 of the drawings is a cross-sectional view of the syringe of this invention in its post operational state.

FIG. 3 of the drawings is an isolated view of the needle assembly of this invention.

FIG. 3(a) is a cross-sectional view along line A—A of FIG. 3, illustrating sacrificial support means and a passageway in the needle assembly.

FIG. 4 of the drawings is a side view of the deformable base.

FIG. 4(a) is a cross-sectional view along line B—B of FIG. 4.

FIG. 5 of the drawings is a side view of the energy storage means.

FIG. 6 of the drawings is a side view of the needle or cannula.

FIG. 7 of the drawings is a side view of the absorbent material.

FIG. 8 of the drawings is a cross-sectional view of the rupturable boot.

FIG. 8(a) is a view along line C—C of FIG. 8, showing a thin web of the rupturable boot.

FIG. 9 of the drawings is a side view of a transparent barrel of this invention.

FIG. 9(a) is an enlarged cross-sectional view of the encircled area of FIG. 9, illustrating a wedge in the needle end of the barrel FIG. 9(b) is a view along line D—D of FIG. 9, showing plunger mating on the operating end of the barrel and finger support means.

FIG. 10 of the drawings is a side view of a plunger in accordance with this invention.

FIG. 10(a) is a view along line E—E of FIG. 10, showing mating on the plunger for the rupturable boot and showing needle capturing means.

FIGS. 16, 17, 18, 19, 20, 21, 22, and 23 of the drawings are cross-sectional views of the apparatus of this invention showing the sequence of operation, after the injection cycle.

FIG. 24 of the drawings is a cross-sectional view of a plunger in a different embodiment of this invention.

FIG. 24(a) is a view along line G—G of FIG. 24, showing a second embodiment of entrapment means for this invention.

FIG. 25 of the drawings is a cross-sectional view similar to FIG. 24 showing the entrapment of a needle therein.

DETAILED DESCRIPTION

Figure 11:
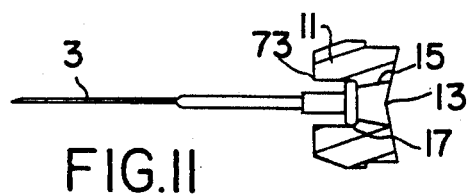
FIGS. 11, 12, and 13 of the drawings are cross-sectional subassembly views illustrating the assembly of the needle, base, barrel, needle assembly, absorbent means, and energy storage means.

In accordance with this invention it has been found that a syringe may be provided for normal operation but, which upon completion of normal operation and continued movement of a plunger, results in a triggering of the needle or cannula to project such needle harmlessly into the plunger of the syringe. Once trapped inside the plunger of the syringe the needle is no longer subject to accidental pricking or poking of human tissue thus minimizing the likelihood of transfer of contagious disease which may be carried by fluids contained within such needle. Various other advantages and features will become apparent from a reading of the following description given with reference to the various figures of drawing.

FIGS. 1 and 2 of the drawings illustrate the syringe 1 of this invention with the needle 3 illustrated in FIG. 1 in its normal pre-injection position. FIG. 2 of the drawings, however, shows the net result of this invention wherein the needle 3 has been trapped and rendered harmless after the injection has taken place, and the plunger has been locked within the barrel of the syringe. The syringe 1 in accordance with this invention has relatively few components, which along with their function, will now be described with reference to the drawings in sequence beginning with FIG. 1.

The syringe 1 has a barrel 5 and a plunger 7 mounted therein. The needle 3 is contained within a needle assembly 9, which is fixed to barrel 5 by ultrasonic welding means or other permanent attaching means.

Needle 3 has an enlarged head 13 mounted within deformable base 11. Enlarged head 13 has a wedge portion 15 and a circular flange portion 17. By appropriately positioning the enlarged head 13 within deformable base 11, the geometries of the flange portion and wedge portion of enlarged head 13 lock such enlarged head portion 13 within deformable base 11, while also creating a liquid tight seal between needle head 13 and deformable base 11.

Needle assembly 9 has contained therein energy storage means 21 within a passageway 23. Enlarged needle head 13 has a contacting portion 25 which contacts energy storage means 21. Sacrificial support means 31 position deformable base 11 within needle assembly 9.

Plunger 7 has a hollow 41 therein and is terminated by a rupturable boot 43 which is fluid impermeable for movement of a fluid in barrel 5 during ordinary injection. Rupturable boot 43 is illustrated as having been ruptured in FIG. 2.

Preferably, plunger 7 has an enlarged compression section at thumb push 45 which, upon completion of a compression stroke, is locked within a mating head portion 47 of barrel 5. Plunger 7 has needle capturing means 49 therein which is illustrated in FIG. 2 as preventing the release of needle 3 from plunger 7. Also illustrated in FIGS. 1 and 2 is an absorption means 51, such as cotton, to collect any fluids which may drain from needle 3 after the capture thereof.

Reference will now be made to FIGS. 3 through 10(a) to more particularly illustrate the components of this invention as described above.

FIG. 3 of the drawings is an isolated view of the needle assembly 9 of this invention. Sacrificial support means 31 and passageway 23 are illustrated in partial phantom.

FIG. 3(a) is a cross-sectional view along the line A—A of FIG. 3, further illustrating sacrificial support means 31 and passageway 23 within needle assembly 9.

FIG. 4 of the drawings is a side view of deformable base 11. A preferred material for base 11 is an elastomer. As seen in FIG. 4, counterbore 73 and thrubore 75 are provided for proper positioning of the needle in the deformable base.

FIG. 4(a) is a cross-sectional view along the line B—B of FIG. 4 further illustrating deformable base 11.

FIG. 5 of the drawings is a side view of the energy storage means 21 illustrated as a spring.

FIG. 6 of the drawings is a side view of needle 3 or cannula. Contactor 25, circular flange 17 and enlarged head 13 with wedge portion 15 are illustrated. Also illustrated in phantom is the hollow portion 16 of the needle.

FIG. 7 shows a side view of absorption means 51 with mounting hole 77.

FIG. 8 of the drawings is a cross-sectional view of the rupturable boot 43.

FIG. 8(a) is a view along the line C—C of FIG. 8 further illustrating rupturable boot 43, with a thin web 79 to aid in the rupturing process. The thickness of web 79 is selected to withstand normal dynamic pressures within syringe 1, as shown in FIG. 1, but allows relative ease in the puncturing of boot 43 by enlarged needle head 13, as shown in FIG. 6.

FIG. 9 of the drawings is a side view of a transparent barrel 5 of this invention, illustrating a 10 cc device.

FIG. 9(a) is an enlarged cross-sectional view of the encircled area of FIG. 9 showing barrel wedge 71.

FIG. 9(b) is a view along the line D—D of FIG. 9 of barrel 5. Mating head portion 47 of barrel 5 is illustrated in phantom, while finger support flange 81 is shown as a full view looking towards the back of the syringe.

FIG. 10 of the drawings is a side view of plunger 7 in accordance with this invention, with capturing means 49 illustrated in partial phantom therein.

FIG. 10(a) is a view along the line E—E of FIG. 10 of plunger 7, further illustrating capturing means 49 within plunger 7.

Given the eight components described above, assembly in four steps is required to produce the syringe. FIGS. 11 through 14 illustrate these four steps so as to result in a finished product. With reference to figure the first assembly step is accomplished by inserting needle 3 into deformable base preferably from the thrubore side. Once inserted, circular flange 17 is positioned into counterbore 73 which blocks needle movement in one direction, since thrubore 75, as shown in FIG. 4, is slightly smaller in diameter than flange 17. Needle wedge 15 expands thrubore 75, as seen in FIG. 4, creating a liquid tight seal between needle head 13 and base 11 as shown in FIG. 11, while also blocking needle movement in the opposite direction. With needle 3 blocked into base 11, assembly step 2 is next accomplished.

Figure 12:
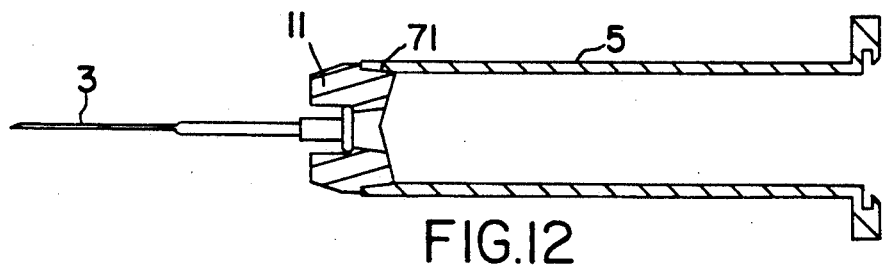

In the second step of the assembly process, the subassembly in FIG. 11 is inserted into the wedged end of barrel 5. When base 11 is completely inserted as shown in FIG. 12, barrel wedge 71 compresses base 11 circumferentially in the direction of needle head 13, and a liquid tight seal is produced between base 11 and barrel 5.

Figure 13:
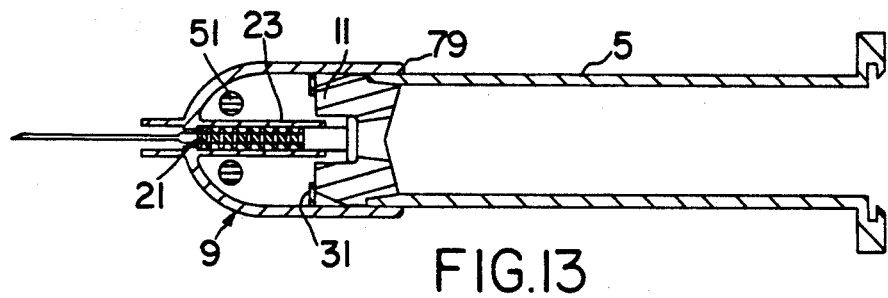

To complete assembly of needle assembly 9 with barrel 5, assembly step 3 is accomplished by first placing absorbent material 51 over passageway 23 in needle assembly 9, as shown in the subassembly of FIG. 13. Energy storage means 21 is then inserted into passageway 23. The preferred embodiment of energy storage means is a spring. Needle assembly 9 is then fixed to barrel 5 by threading needle 3 through the center of spring 21 in passageway 23 and compressing spring 21 until needle assembly 9 is in a position where sacrificial support means 31 are firmly against base 11 and overlap 79 between needle assembly 9 and barrel 5 is created. During this assembly step significant energy is transferred to energy storage means 21. Permanent joining between needle assembly 9 and barrel 5 is accomplished by ultrasonic welding around the circumference at overlap 79, or other permanent attaching means.

Figure 14A:
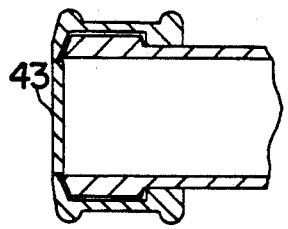
FIG. 14(a) is an enlarged view of the encircled area of FIG. 14, showing more clearly the rupturable boot assembled on the plunger.
Figure 14:
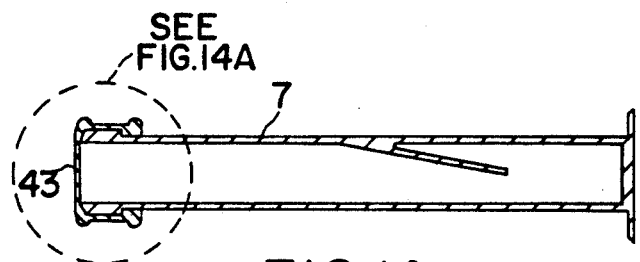
FIG. 14 of the drawings is a cross-sectional view of the plunger of this invention, showing assembly of the rupturable boot on the plunger.
Figure 15:
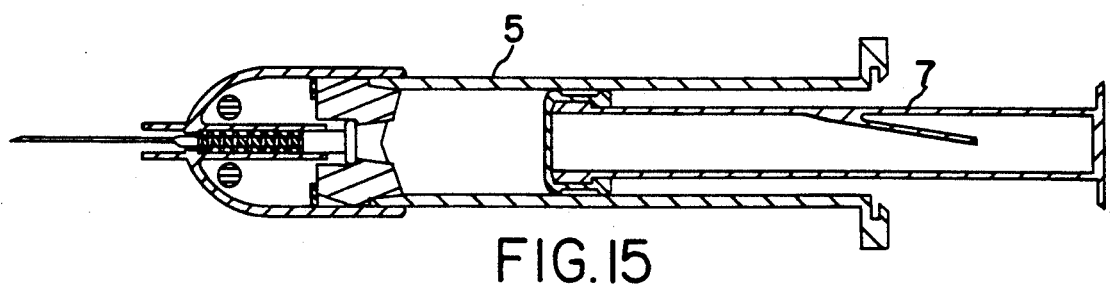
FIG. 15 of the drawings is a view of the completed assembly of the syringe

In the final step of assembly, rupturable boot 43 is placed onto plunger 7 as shown in FIGS. 14 and 14(a). Plunger 7 is then inserted into barrel 5, to complete the assembly as shown in FIG. 15. It will be apparent to those in the art that there exists other possible sequences of assembly other than those described that can be used to produce the completed assembly as shown in FIG. 15, producing the same syringe ready for operation.

The sequence of operation will now be described with regard to FIG. 1 and FIGS. 16 through 23. As can be seen, FIG. 1 is a cross-sectional view of safety syringe 1. For normal syringe operating forces safety syringe 1 operates as any conventional syringe. For use, the syringe is filled from an ampule in a normal manner, as standard procedure dictates. Once filled, the injection cycle is accomplished, again according to standard practice. At completion of the injection cycle, plunger 7 is just mating with base 11, as shown in FIG. 16, and all fluids, which can be, are expended from syringe 1. Before the syringe is released, or discarded, by the user, the needle retraction cycle should be accomplished.

At the beginning of the needle retraction cycle, syringe 1 is usually held between the index finger and the middle finger at support flange 81, with the thumb resting on thumb push 45, presumably the same as the syringe was held at completion of the injection cycle. Plunger 7 is just mated with base II at rupturable boot 43, as shown in FIG. 16.

With reference to FIG. 17, force is applied between finger support flange 81 and thumb push 45. This force is transmitted along plunger 7 to deformable base 11 and sacrificial support means 31. As the force increases sufficiently, the liquid tight seal between barrel 5 and deformable base is broken, and sacrificial support means 31 begin to fracture.

As shown in FIG. 18 further force is applied at plunger 7. Sacrificial support means 31 are severed and deformable base II moves forward, further compressing energy storage means 21. Deformable base 11 moves forward until circular flange 17, on needle head 13 which is in translation with base 11, comes into contact with the end of needle passageway 23.

With reference now to FIG. 19 enlarged needle head 13 is blocked by passageway 23, and continued force at plunger 7 causes deformable base 11 to deform and move around circular flange 17 on enlarged needle head 13. As deformable base 11 moves forward, enlarged needle head 13 begins to protrude from base 11 and come into contact with web 79 of rupturable boot 43 on plunger 7. Continued force causes further translation of base 11 and enlarged needle head 13 to penetrate web 79 of rupturable boot 43, positioning enlarged needle head 13 just inside hollow 41 of plunger 7 while circular flange 17 remains embedded within deformed base 11, as shown in FIG. 19.

With reference to FIG. 20, continued translation of deformable base 11 cause circular flange 17 to eventually lose contact with deformable base 11, creating a trigger-like release of circular flange 17. Upon this trigger-type action, energy stored within energy storage means 21 is released and imparted to needle 3 to project needle 3 into hollow 41 of plunger 7, as illustrated in FIG. 21.

Referring now to FIG. 22, it is seen that needle 3, at its enlarged head 13, contacts capturing means 49 which deforms to permit enlarged needle head 13 to pass through the constriction formed by capturing means 49. This is further illustrated in FIG. 23 where needle 3 is shown captured within hollow 41 of plunger 7. At this point, it should be noted that plunger thumb push 45 has been locked within the mating section 47 of barrel 5. As syringe 1 is tilted downward, fluids remaining in needle 3 flow within hollow 41, down the exterior side of passageway 23 to absorbent means 51 where the fluids are absorbed and prevented from being released from the interior of syringe 1.

An optional capturing means is illustrated in FIG. 24 wherein a plunger 61 has a constricted head portion 63 adjacent to a contacting portion 65. As illustrated in FIG. 25, needle 3 is lodged within the constricted portion 63 as a result of needle 3 being projected from deformable base 11. FIG. 24(a) is a view of plunger 61 taken along line G—G of FIG. 24 showing the constricted head portion 63. Other capturing means may also by utilized.

It is thus seen that this invention provides a novel syringe apparatus which is operable by a single hand and which upon completion of injection captures the utilized needle and renders such harmless within the plunger of the syringe. As various other advantages and features will become apparent to those of skill in the art from a reading of the foregoing description which is exemplary in nature, such modification and variations are embodied within the scope of this invention as defined by the following appended claims.

We claim:

1. A syringe apparatus, comprising:
   a barrel;
   a plunger movable within said barrel;

a needle assembly mounted on said barrel;

a deformable base interconnecting said barrel and said needle assembly;

sacrificial support means in said needle assembly for positioning said deformable base;

a hollow needle containment tube formed in said needle assembly defining a passageway extending between said deformable base and an opposite side of said needle assembly;

energy storage means within said passageway;

a hollow needle passing through said passageway;

an enlarged head on said needle within said needle assembly engaged between said deformable base said energy storage means; and a rupturable boot on said plunger for moving a fluid within said barrel through the hollow of said needle when said plunger is moved through said barrel toward said needle assembly;

whereby when said plunger moves through said barrel toward said needle assembly a fluid is moved from said barrel through the hollow of said needle and when said boot contacts said deformable base continued movement thereof moves said deformable base downwardly severing said sacrificial support means with continued movement until such time as sufficient force is imparted to said rupturable boot by said enlarged head of said needle to rupture said rupturable boot, said deformable base then releasing said needle with said enlarged head due to the force applied thereto by said energy storage means to project said needle with said enlarged head into the interior of said plunger.

2. The apparatus according to claim 1 wherein said enlarged head is wedge-shaped converging to an enlarged locking portion locked within said deformable base.

3. The apparatus according to claim 1 wherein said barrel has a termination on the end opposite said needle assembly and said plunger has an enlarged operating head, said enlarged operating head being receivable within said termination.

4. The apparatus according to claim 1 wherein said plunger is hollow on the interior thereof for receipt of said needle and said enlarged head and further comprising means within said plunger for capturing said needle and said enlarged head when it is projected thereinto.

5. The apparatus according to claim 4 further comprising an absorbent material near said rupturable boot to prevent release of any fluid contained in said needle.

6. The apparatus according to claim I wherein said energy storage means is a spring.

7. A syringe apparatus, comprising:
a barrel;
a plunger movable within said barrel;
a needle assembly fixed to said barrel;
a deformable base positioned between said barrel and said needle assembly;
sacrificial support means in said needle assembly for positioning said deformable base;
a hollow needle containment tube formed in said needle assembly defining a passageway extending between said deformable base and an opposite side of said needle assembly;

energy storage means within said passageway;

a hollow needle passing through said passageway;

an enlarged head on said needle within said needle assembly engaged between said deformable base said energy storage means; and a rupturable boot on said plunger for moving a fluid within said barrel through the hollow of said needle when said plunger is moved through said barrel toward said needle assembly;

whereby when said plunger moves through said barrel toward said needle assembly a fluid is moved from said barrel through the hollow of said needle and when said boot contacts said deformable base continued movement thereof moves said deformable base downwardly severing said sacrificial support means with continued movement until said enlarged head of said needle ruptures said rupturable boot, said deformable base then releasing said needle with said enlarged head to project said needle with said enlarged head into the interior of said plunger.

8. The apparatus according to claim 7 wherein said enlarged head is wedge-shaped converging to an enlarged locking portion locked within said deformable base.

9. The apparatus according to claim 7 wherein said barrel has a termination on the end opposite said needle assembly and said plunger has an enlarged operating head, said enlarged operating head being receivable within said termination.

10. The apparatus according to claim 7 wherein said plunger is hollow on the interior thereof for receipt of said needle and said enlarged head and further comprising means within said plunger for capturing said needle and said enlarged head when it is projected thereinto.

11. The apparatus according to claim 7 further comprising an absorbent material near said rupturable boot to prevent release of any fluid contained in said needle from the interior of said syringe.

12. The apparatus according to claim 7 wherein said energy storage means is a spring.

13. A syringe comprising:
a barrel having a first end and an opposite second end;
a plunger having a forward end and movable within the barrel from the second end of the barrel towards the first end, the plunger having a hollow interior communicating with the forward end;
a hollow needle having a pointed front extending through the first end of the barrel and a rear end received within the barrel;
energy storage means positioned in the barrel between the first end and the opposite second end in engagement with the needle; and
an absorbent material within said syringe;
whereby a fluid is moved from within the barrel through the needle as the plunger moves through the barrel to then allow the energy storage means to eject the needle into the interior of the plunger where any excess liquid material is absorbed by said absorbent material.

* * * * *